(12) United States Patent
Horber

(10) Patent No.: US 7,303,585 B2
(45) Date of Patent: *Dec. 4, 2007

(54) ENDOPROSTHESIS FOR A SHOULDER JOINT

(76) Inventor: Willi Horber, Turbinenstrasse 12, Zürich, CH-8005 (CH)

( * ) Notice: Subject to any disclaimer, the term of this patent is extended or adjusted under 35 U.S.C. 154(b) by 0 days.

This patent is subject to a terminal disclaimer.

(21) Appl. No.: 10/438,836

(22) Filed: May 16, 2003

(65) Prior Publication Data

US 2004/0030396 A1   Feb. 12, 2004

Related U.S. Application Data

(63) Continuation of application No. PCT/CH01/00676, filed on Nov. 16, 2001.

(30) Foreign Application Priority Data

Nov. 16, 2000  (CH) ................... 2234/00
Nov. 16, 2000  (CH) ................... 2235/00

(51) Int. Cl.
*A61F 2/40*   (2006.01)
*A61F 2/30*   (2006.01)
(52) U.S. Cl. .................. 623/19.14; 623/18.11
(58) Field of Classification Search .. 623/19.11–19.14, 623/21.15–21.17, 22.4–22.46, 18.11
See application file for complete search history.

(56) References Cited

U.S. PATENT DOCUMENTS

| 3,815,157 A | 6/1974 | Skorecki et al. |
| 4,011,603 A | 3/1977 | Steffee |
| 4,318,190 A | 3/1982 | Cortesi |
| 4,528,702 A | 7/1985 | Frey |
| 5,314,485 A | 5/1994 | Judet |
| 5,458,649 A | 10/1995 | Spotorno et al. |
| 5,522,903 A | 6/1996 | Sokolow et al. |
| 5,702,457 A | 12/1997 | Walch et al. |
| 5,702,471 A | 12/1997 | Grundei et al. |
| 5,741,335 A | 4/1998 | Gerber et al. |

(Continued)

FOREIGN PATENT DOCUMENTS

DE   195 09 037 C1   9/1996

(Continued)

OTHER PUBLICATIONS

Search Report for PCT/CH00/00515 dated Jan. 30, 2001 (cited in U.S. Appl. No. 10/088,630.

(Continued)

*Primary Examiner*—David J. Isabella
(74) *Attorney, Agent, or Firm*—Buchanan Ingersoll & Rooney PC

(57) ABSTRACT

A rotation-symmetrical articulation chamber is formed in the shaft head of an endoprosthesis. An axial articulation member is disposed in this chamber. The articulation member axis and the axis of rotation are perpendicular relative to each other. A joint neck can be pivoted about the axis of rotation and the articulation member axis at any selected angle of inclination or rotation. Clamping surfaces that are disposed at an angle to the axis of rotation are rotation-symmetrical or planar and interact with articulation surfaces of the articulation member that can also be rotation-symmetrical.

26 Claims, 3 Drawing Sheets

U.S. PATENT DOCUMENTS

| | | |
|---|---|---|
| 5,888,207 A | 3/1999 | Nieder et al. |
| 6,093,208 A | 7/2000 | Tian |
| 6,102,951 A | 8/2000 | Sutter et al. |
| 6,197,063 B1 | 3/2001 | Dews |
| 6,228,120 B1 | 5/2001 | Leonard et al. |

FOREIGN PATENT DOCUMENTS

| | | |
|---|---|---|
| DE | 19548154 | 6/1997 |
| DE | 196 16 059 A1 | 10/1997 |
| DE | 29918589 | 3/2000 |
| EP | 0 024 442 A1 | 8/1979 |
| EP | 0 208 578 A1 | 6/1986 |
| EP | 0 351 545 A1 | 6/1989 |
| EP | 0 532 440 A1 | 3/1993 |
| EP | 0 663 193 A1 | 12/1993 |
| EP | 0 586 335 A1 | 3/1994 |
| EP | 0 669 117 A1 | 8/1995 |
| EP | 0 679 375 | 11/1995 |
| EP | 0 712 617 A1 | 11/1995 |
| EP | 0 884 032 A1 | 6/1997 |
| EP | 0 850 609 | 12/1997 |
| EP | 0 903 128 | 3/1999 |
| EP | 0 963 741 A2 | 5/1999 |
| FR | 2 321 871 | 8/1975 |
| FR | 2 773 469 | 7/1999 |
| WO | WO 98/46172 | 10/1998 |
| WO | WO 99/34756 | 7/1999 |
| WO | WO 00/01327 | 1/2000 |
| WO | WO01/22905 | 4/2001 |

OTHER PUBLICATIONS

Search Reports for PCT/CH01/00676 dated Mar. 11, 2002 and Apr. 16, 2002.

Search Reports for PCT/CH01/00674 dated Feb. 26, 2002 and Jan. 16, 2003.

Search Report for PCT/CH01/00675 dated Feb. 26, 2002.

ENDOPROSTHESIS FOR A SHOULDER JOINT

CROSS REFERENCE TO RELATED APPLICATIONS

This application claims priorities under 35 U.S.C. §119 to Swiss Application 2234/00 filed in Switzerland on Nov. 16, 2000, and to Swiss Application 2235/00 filed in Switzerland on Nov. 16, 2000, and as a Continuation Application under 35 U.S.C. §120 to PCT/CH01/00676 filed as an International Application on Nov 16, 2001 designating the U.S., the entire contents of which are hereby incorporated by reference in their entireties.

This application is also related to U.S. Patent Application entitled "Endoprosthesis For A Shoulder Joint", Ser. No. 10/088,630, filed Mar. 20, 2002, and issued as U.S. Pat. 6,749,637, to U.S. Patent entitled "Joint Prosthesis", issued as U.S. Pat. No. 6,818,019, filed on even date herewith and to U.S. Patent entitled "Joint Prosthesis", issued as U.S. Pat. No. 7,108,719, filed on even date herewith each of which is hereby incorporated herein by reference in its entirety.

BACKGROUND

1. Field

The invention relates to an endoprosthesis for a shoulder joint. The endoprosthesis comprises an axial shaft piece for insertion, into the humerus and a neck piece articulated by an articulation member on the shaft piece. The neck piece comprises an axial joint neck alignable with the neck piece to receive a joint head. Fixing means are also provided for fixing the neck piece in a selected alignment and a joint head with a first articulation surface. This articulation surface co-operates with a second artificial or the natural articulation surface on the shoulder. The prosthesis therefore if required also includes a prosthesis part with the artificial second articulation surface.

2. Background Information

A shoulder joint prosthesis is known from EP-A-712 617. It comprises a shaft which is adapted to be anchored in the humeral canal and a cap with a substantially hemispherical profile. The cap can co-operate with the joint socket of the shoulder. In this shoulder joint prosthesis, the shaft comprises an articulation seating with a hemispherical base. A ball is disposed in the articulation seating and comprises means to receive the cap. In addition, locking means are provided, particularly grub screws, which enable the locking of the ball in a specific angular position relative to the axis of the shaft.

This shoulder joint prosthesis, thanks to the ball joint between the shaft and the joint neck, allows stepless regulation of the inclination and rotation of the neck axis. A disadvantage of this prosthesis is that it is relatively complex to make spherical surfaces and the fixing of spherical surfaces with respect to a concentric spherical surface is difficult.

FR 2 773 469 discloses a shoulder joint prosthesis with a shaft piece, a directional member pivotable thereon and carrying a ball cap. In this prosthesis, the metaphysal shaft piece end is provided with a hemispherical recess with a screwthreaded bore in the base thereof. The recess and screwthreaded bore are aligned to a neck axis, the angle of which to the shaft axis is preselected. A pivotable directional member fits in the recess and has a hemispherical surface at its humeral end, said hemispherical surface being concentric with the hemispherical surface of the recess. The directional member has an axial bore with a hemispherical base. A screw with a spherical head is guided with the shank forward into the bore, the screwthreaded portion of the shank being pushed through a conical bore in the hemispherical base of the directional member and screwed into the screwthreaded bore in the shaft piece. The centers of the spherical surfaces of the recess in the shaft piece, inner and outer spherical surfaces on the directional member and the spherical surface of the screw head are situated at a common central point when the screw is tightened. As a result of this construction, the intermediate member is adapted to be pivotable steplessly in all directions relative to the shaft piece and simultaneously rotatable.

A disadvantage of this prosthesis is that the four spherical surfaces must have a common center and therefore have to be made with the maximum precision to ensure a sufficient hold between the spherical surfaces.

DE-U-299 18 589.3 discloses a shoulder joint prosthesis which avoids this problem of extreme precision for the spherical surfaces. This prosthesis has a shaft piece for implanting in the humerus with a shaft head. In the area of the shaft head an articulation surface is formed on which a rotary member is disposed. This is rotatable relatively to the shaft piece about a first axis. A directional member is articulated on the rotary member and extends along a directional axis and is rotatable about a second axis with respect to the rotary member. The second axis extends transversely of the first axis and transversely of the directional axis. The latter is thus steplessly pivotable in all directions. The rotary member and the directional member are each fixable in a selectable position. A head cap is connectable to the shaft piece via the directional member and the rotary member. Articulation or contact surfaces between the shaft piece and the rotary member allow only a relative movement between the shaft piece and the rotary member about their common first axis. Articulation or contact surfaces between the rotary member and the directional member allow only a relative movement between the rotary member and the directional member about the common second axis as rotation center.

A disadvantage of this endoprosthesis is that at least two intermediate members are required between the shaft piece and the cap.

SUMMARY

The invention is directed to a shoulder joint prosthesis wherein the neck axis is also fixable in respect of inclination and rotation in a selectable angular position relative to the shaft axis. At the same time, as in the case of the ball joint, the joint neck can be articulated on the shaft piece directly by way of a single articulation member. This articulation member and the surfaces co-operating therewith on the shaft piece can require less precision than spherical surfaces.

According to the invention, the articulation member comprises at least one axial-symmetrical articulation surface, the axis of symmetry of which is perpendicular to the joint neck axis. This articulation surface co-operates with at least one clamping surface on the shaft piece, which is substantially rotationally symmetrical to a rotational axis and the rotational axis of which is perpendicular to the axis of symmetry of the articulation surface. This clamping surface can in particular be formed substantially planar and be perpendicular to the rotational axis.

Advantageously, two opposite articulation surfaces are of axially symmetrical construction and co-operate with two only rotationally symmetrical and non-spherical clamping surfaces. However, one of the articulation surfaces can be spherically symmetrical and co-operate with a similar surface. Alternatively, just one of the cooperating surfaces can be spherically symmetrical while the other is only rotationally symmetrical.

The clamping surfaces advantageously substantially correspond to the form of rotation of the articulation member about the neck axis. The articulation member advantageously has, both on the side facing the shaft piece and the side facing the ball cap, articulation surfaces situated opposite one another. These can be of different constructions, but advantageously have the same axis of symmetry. The articulation surfaces are advantageously rotationally symmetrical, but can also be polyhedra approximating a rotational surface. Simple forms are substantially cylindrical, conical or toroidal. Mixed forms of these three forms are also possible. The surfaces can be flat and smooth, rough or grooved. Points or burrs can be formed on the surfaces. The articulation surfaces can also have free shapes, for example be corrugated. Deviations from a simple cylinder on a flat clamping surface have the advantage that centering of the articulation member takes place on clamping.

Advantageously, the articulation surfaces can be, at least in angular zones within the pivoting angles of the joint neck, rotationally symmetrical to the axis of symmetry about the axis of symmetry of the articulation surfaces or are polyhedra approximating a surface rotationally symmetrical to the axis of symmetry.

If the articulation surfaces are formed by a number of edges or if they have burrs, points or the like, then when the articulation member is clamped fast the articulation surface catches with the clamping surfaces. Similarly, the clamping surfaces can have edges, points or burrs so that they tooth with the articulation surfaces. Advantageously, such edges are formed on both co-operating surfaces. A toothing can also advantageously be produced by the provision of interengaging grooves and burrs or corrugation structures on the articulation surface and the clamping surface.

Two opposite clamping surfaces are advantageously formed on the shaft piece, and between them an articulation chamber is formed to receive the articulation member. For this purpose, the shaft piece advantageously comprises a shank for insertion in the humerus bone, a metaphysal shaft head and a cover adapted to be fitted on to the shaft head. The clamping surfaces are formed on the shaft head and on the cover. The cover is advantageously a screw-on cover. This enables the distance between the two clamping surfaces on the shaft piece and on the cover to be adjusted easily. Other connections are also possible, however, for example hinge/screw connections, insertion of the cover along a rail parallel to the clamping surface, fitting the cover parallel to the rotational axis on to the shaft head and fixing with bolts or screws extending transversely to the fitting direction, or an integrally fixed connection of the cover and shaft head.

In addition or alternatively to such a first clamping means on the shaft piece, with which the articulation member can be pressed towards the shaft axis against a clamping surface on the shaft head, a second clamping means can advantageously be provided. A second clamping means can include at least one screw with which the articulation member is clamped relative to one of its surrounding surfaces. The screw can be screwed into the articulation chamber from outside.

Advantageously, however, a screwthreaded bore is provided which extends through the articulation member and through which a screw can be screwed as a second clamping means. Since the joint neck is readily accessible, this bore is advantageously on the joint neck axis. The bore can simply extend through the articulation member, in which case the joint neck is formed as a screw. In an exemplary embodiment, however, the screwthreaded bore can also extend through the joint neck and a screw can be screwed through a one-piece neck piece with an articulation member and joint neck.

Advantageously, the distance between the clamping surfaces is adjustable in order at least provisionally to fix the articulation member.

Advantageously, clamping surfaces or clamping edges are formed on the shaft head and the cover. The articulation chamber between the clamping surfaces and the clamping edges can be formed in the shaft head and/or in the cover.

BRIEF DESCRIPTION OF THE DRAWINGS

Exemplified embodiments of shoulder joint prostheses according to the invention and having advantageous features are described with reference to the accompanying diagrammatic and simplified drawings wherein.

DETAILED DESCRIPTION OF THE DRAWINGS

Figure 1:
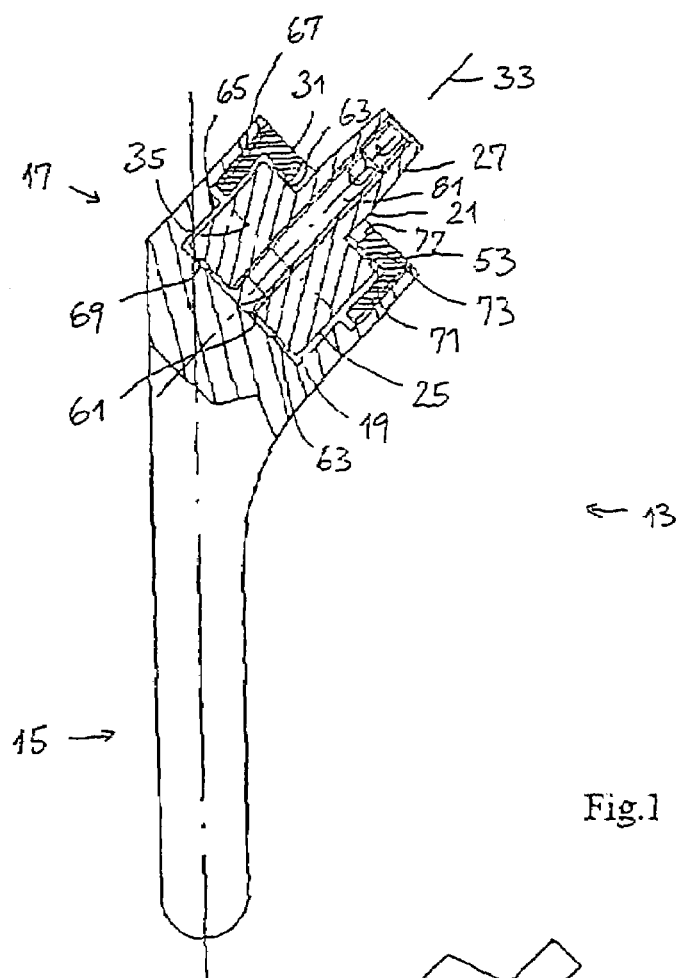
FIG. 1 shows a shaft piece of an endoprosthesis according to an exemplary embodiment of the invention with a neck piece disposed therein, in front elevation and in section in the articulation zone.

FIG. 1 shows an exemplary endoprosthesis without articulation surfaces of the shoulder joint. The shaft piece 13 comprises a shank 15, a shaft head 17 and a cover 53. An articulation member 25 is articulated in the shaft head 17 and together with the joint neck 27 forms a neck piece 21. An articulation chamber 19 is formed in the shaft head 17. The articulation chamber 19 has a flat base 61 with a circular rib 0.63 and a cylindrical wall 65. An internal screwthread 67 is formed in the wall 65. A cover 53 is screwed into said inner screwthread. A clamping plate 31 is formed on the cover 53 and has a flat clamping surface 71 towards the top articulation surface 73 of the articulation member 25. A circular rib 63 is formed on the clamping surface 71. The articulation member 25 is cylindrical and has two peripheral ribs 69.

By slight tightening of the cover 53, the articulation member is clamped between the two clamping surfaces, namely the clamping surface 71 on the cover 53 and the base surface 61 on the shaft head 17. Depending on the clamping force, the neck piece 21 can be pivoted about the pivot axis 35, which is the axis of symmetry of the articulation surfaces, and be rotated about the axis 33 of the articulation chamber 19. A circular conical central opening 77 is provided in the clamping plate 31. The joint neck 27 extends out of the articulation chamber 19 through said opening 77. The opening 77 is so dimensioned that the joint neck 27 is pivotable to a sufficient degree in any direction.

Extending through the joint neck 27 is a bore with an internal screwthread into which a grub screw 81 with a sharp point is screwed. By screwing in the grub screw, the point can be pressed against the base 61 and dug into the latter. As a result there is a definitive fixing of the neck piece 21 on the shaft piece 13. To secure the grub screw 81, a second screw is screwed into the screwthread and pressed against the grub screw.

Figure 2:
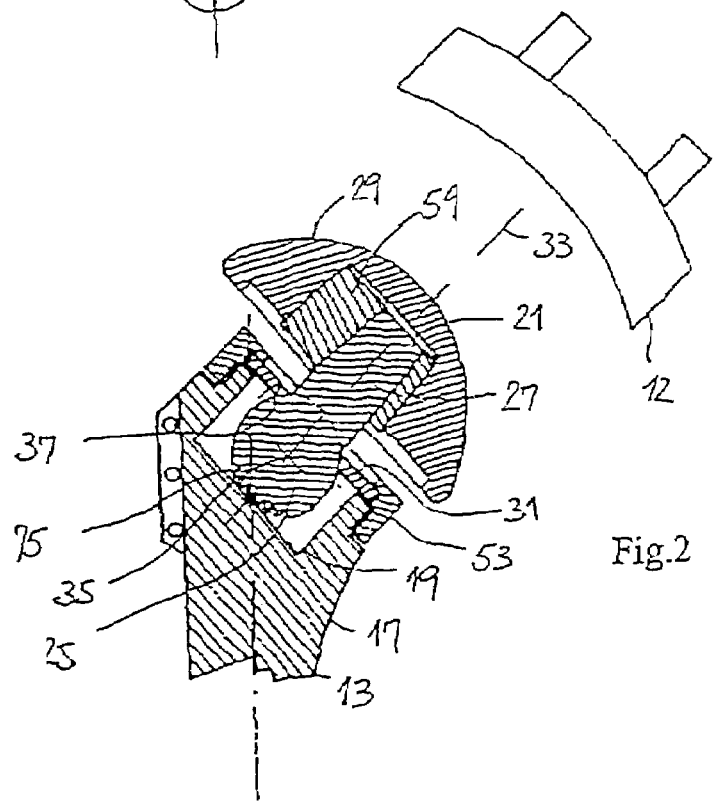
FIG. 2 is a partial section through an endoprosthesis according to an exemplary embodiment of the invention with a rotatable clamping plate and with an eccentric ring and a head cap, and a joint socket.

FIG. 2 shows a second exemplified embodiment in which the articulation member 25 also has a cylindrical shape. The articulation chamber 19 is also cylindrical here. The cylindrical axis of the articulation member 25 extends perpendicularly to the neck axis 33, while the cylindrical axis of the articulation chamber 19 is perpendicular to the cylindrical axis of the articulation member 19. The base of the articulation chamber 19 is planar and perpendicular to its cylindrical axis.

The articulation member 25 is just long enough for the edges of its end faces to touch the wall of articulation chamber 19 without clamping and the articulation member is turnable always centered in the articulation chamber.

This rotation is also carried out by the clamping plate 31. It bears by a straight opening edge 37 against the cylindrical surface and is circular. The clamping plate 31 is fixed by a cap nut 53 on the shaft head 17 and is freely rotatable between the same. The steplessly adjustable deviation of the neck axis 33 from the cylindrical axis of the articulation chamber 19 can thus be aligned steplessly through 360° perpendicularly to the plane of the bone sectional surface. This gives the same freedom of alignment of the neck axis after the style of a ball joint as a real ball joint. The articulation surface 75*a* of the articulation member 25 facing the base of the articulation chamber 19 is grooved so that edges are formed on the cylindrical surface and press furrows into the planar base of the articulation chamber 19 when the cap nut 53 is tightened. As a result of this intercatching of the articulation member 25 and the articulation chamber, both turning about the cylindrical axis of the articulation chamber 19 and also about the cylindrical axis 35 of the articulation member 25 are blocked. In this exemplified embodiment, the clamping plate can also be inserted from the side between the cap nut 53 and the articulation head. For this purpose the cap nut does not require any screwthread but can, for example, be formed to engage in a groove extending around the articulation chamber. If the clamping plate has a wedge shape and there is a correspondingly angled contact surface on the cap nut, the pressure on the joint head can be obtained by knocking the clamping plate in.

In FIG. 2, in addition, an eccentric ring 59 is pushed on to the joint neck 27. The eccentric ring 59 can be turned about the joint neck axis for adjustment of the eccentricity of the cap 29 with respect to the joint neck 27. An-artificial joint socket 12 is also shown.

Figure 3:
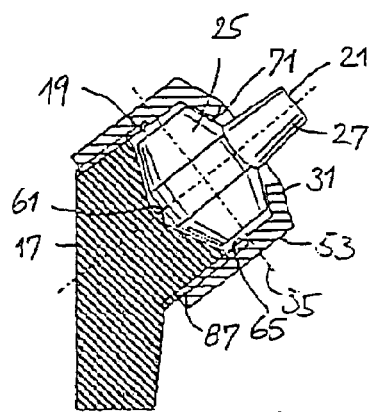
FIG. 3 is a section through the articulation zone of an endoprosthesis according to an exemplary embodiment of the invention with the articulation chamber in a cover and conical articulation and clamping surfaces.

FIG. 3 shows a second exemplified embodiment. The articulation chamber 19 is formed in the cover 53 which is screwed on to an external screwthread 87 formed on the shaft head 17. The articulation member 25 has two oppositely directed frusto-conical surfaces acting as articulation surfaces. The base 61 of the articulation chamber 19 is also frusto-conically concave. The two angles of the co-operating conical outer surfaces correspond to one another complementarily. The clamping plate 31 on the cover 53 also has a frusto-conical clamping surface 71.

The clamping plate 31 can also be constructed in the form of a washer which is pressed by a cap nut 53 against the articulation member 25. It therefore need not be made integrally with the cap nut. The advantage of this is that on tightening of the cap nut 53 a turning of the cap nut is transmitted to a lesser degree to the articulation member 25. The clamping surfaces of the base 61 and/or of the clamping plate 31 can also be formed as one or more complementarily frusto-conically arranged annular edges.

Figure 4:
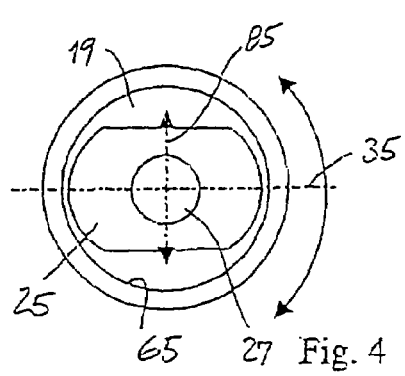
FIG. 4 is a plan view of an exemplary neck piece in the articulation chamber.

FIG. 4 shows how the articulation member 25 is pressed into the cylindrical wall 65 of the articulation chamber 19. The axial ends of the articulation member 25 are constructed to be convexly curved approximately concentrically to the wall 65. To enable the articulation member 25 to pivot (arrow 85) about the pivot axis 35, there must be a distance maintained between the wall 65 and the articulation member 25. Since normally a 10° pivotability is sufficient, the distance can be small.

Figure 5:
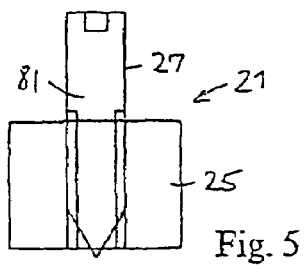
FIG. 5 is a section through an exemplary neck piece with a joint neck constructed as a clamping screw.

FIG. 5 shows the basic possibility of making the joint neck 27, directly in the form of a fixing screw. A screwthreaded bore is provided in the articulation member 25 and the joint neck is screwed into this. A point is formed on the joint neck and is adapted to dig into the base 61 of an articulation chamber by tightening of the screw. The base 61 may have a spherical surface in the corresponding zone so that the point always meets the base surface perpendicularly.

Figure 6:
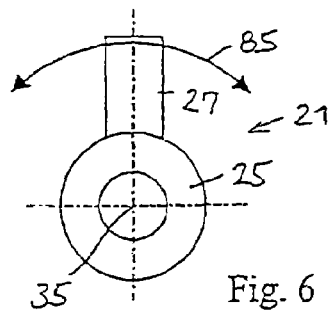
FIG. 6 is an axial view of an exemplary neck piece with conical articulation surfaces.

FIG. 6 shows the pivotability of the neck piece 25 (double arrow 85). A neck piece is shown as in FIG. 3, its articulation member having on both sides of the joint neck 27 a frusto-conical articulation surface in each case.

Figure 7:
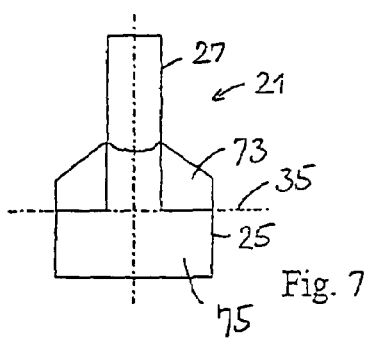
FIGS. 7 and 8 are a side view and axial view of an exemplary neck piece with a cylindrical articulation surface at the bottom and a conical articulation surface at the top.
Figure 8:
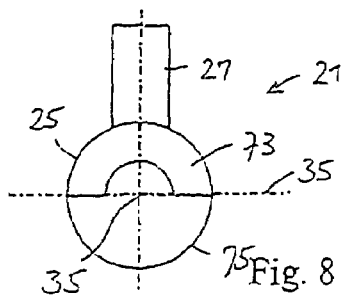

The articulation surfaces need not be identical top and bottom. In FIGS. 7 and 8 a neck piece 21 is shown of which the articulation member 25 has a conical articulation surface 73 at the top and a cylindrical articulation surface 75 at the bottom.

Figure 9:
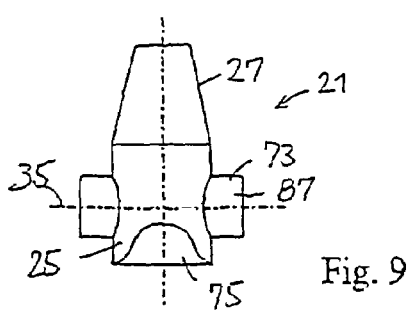
FIGS. 9 and 10 are a side elevation and axial elevation of an exemplary neck piece with the articulation surfaces at the bottom on the joint neck, which is rounded in the form of a barrel, and at the top on a bolt projecting perpendicularly from the joint neck.
Figure 10:
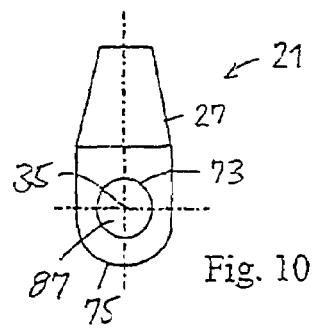

It is possible for the joint neck 27 itself to form part of the articulation member 25. FIGS. 9 and 10 show a neck piece 21 of this kind in which the underside is rounded to be barrel shaped and forms an articulation surface 75. The upper articulation surface 73 is formed on a bolt 87 crossing the joint neck 27.

Figure 11:
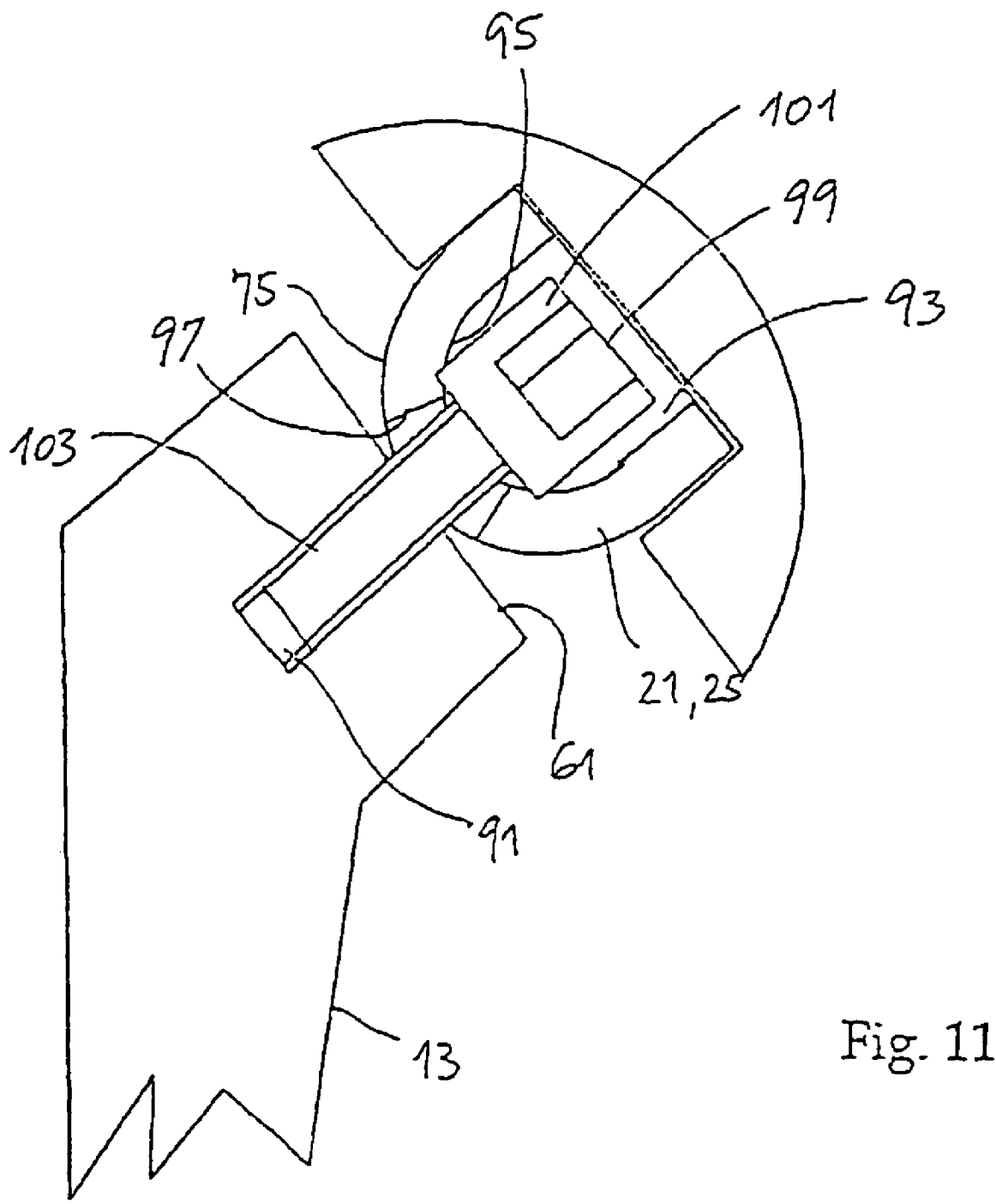
FIG. 11 is a section through an exemplary shaft head part with a neck piece which has a central bore in which the head of a fixing screw fits.

It is also possible to fix the neck piece by means of a central screw in the shaft piece. FIG. 11 shows a shaft piece 13 having a planar clamping surface 61 or a clamping surface structured by edges, points or the like. A screwthreaded bore 91 is provided centrally in the clamping surface 61.

A cylindrical articulation surface 76 of the neck piece 21 bears on the clamping surface 61. The neck piece 21 has transversely of the neck axis a circular cross-section. A cavity bore 93 with a hemispherical base 95 is formed concentrically to the periphery therein. A conical opening 97 opening outwards is provided in the base. A screw 99 fits with a head 101 in the cavity bore 93 and its screwthreaded shank 103 extends through the opening 97 in the base 95 of the cavity bore 93 into the screwthreaded bore 91 in the shaft piece 15. The screw head 101 has a circular edge which on tightening of the screw 99 bears against the hemispherical base and digs into the base. As a result of the pressing force, either the clamping surface 61 or the articulation surface 75 is deformed so that rotation of the neck piece 21 about its neck axis is prevented. Pivoting of the neck piece about the axis of symmetry of the cylindrical articulation surface 75 is prevented by the connection between the screwhead 101 and the neck piece 21. The axis of symmetry of the articulation surface 75 passes through the center of the spherical surface of the base. 95.

It will be appreciated by those skilled in the art that the present invention can be embodied in other specific forms without departing from the spirit or essential characteristics thereof. The presently disclosed embodiments are therefore considered in all respects to be illustrative and not restricted. The scope of the invention is indicated by the appended claims rather than the foregoing description and all changes that come within the meaning and range and equivalence thereof are intended to be embraced therein.

The invention claimed is:

1. An endoprosthesis for a shoulder joint, with a joint socket for anchoring in the shoulder blade glenoid or for pivotal co-operation with the natural glenoid, comprising:
    a shaft piece with a shank and a metaphysal shaft head configured for insertion into a humerus;
    a neck piece articulated with an articulation member to the shaft head and comprising an axial joint neck adapted to be aligned with the neck piece and to receive a head cap;
    fixing means for fixing the neck piece in a selected alignment; and
    a head cap for articulation with the joint socket or the natural glenoid, wherein the articulation member has an articulation surface which is only axially symmetrical and the axis of symmetry of which is perpendicular to a joint neck axis, and wherein the articulation surface co-operates with at least one clamping surface on the shaft piece, said clamping surface being substantially rotationally symmetrical to a rotational axis and/or being substantially planar and perpendicular to the rotational axis, the rotational axis being perpendicular to the axis of symmetry of the articulation surface.

2. An endoprosthesis according to claim 1, wherein the articulation surface is rotationally symmetrical to the axis of symmetry in angular zones within a pivoting angle of the joint neck about the axis of symmetry of the articulation surface.

3. An endoprosthesis according to claim 2, wherein in angular zones within the pivoting angle of the joint neck about the axis of symmetry of the articulation surface, the articulation surface is a polyhedron approximating a surface rotationally symmetrical to the axis of symmetry.

4. An endoprosthesis according to claim 1, wherein the articulation surface is formed by a number or edges.

5. An endoprosthesis according to claim 1, wherein the articulation surfaces of the articulation member which are situated opposite one another in a direction of the joint neck axis are formed differently.

6. An endoprosthesis according to claim 1, wherein at least one articulation surface has substantially a conical shape.

7. An endoprosthesis according claim 1, wherein at least one articulation surface has substantially a cylindrical shape.

8. An endoprosthesis according to claim 1, wherein at least one articulation surface has substantially a toroidal shape.

9. An endoprosthesis according to claim 1, wherein at least one articulation surface has a corrugated surface.

10. An endoprosthesis according to claim 1, wherein the shaft piece has a first clamping means by which the articulation member can be pressed against the shaft piece.

11. An endoprosthesis according to claim 1, wherein a screwthreaded bore extends through the articulation member and a screw can be screwed therethrough as a second clamping means.

12. An endoprosthesis according to claim 11, wherein the joint neck forms the second clamping means.

13. An endoprosthesis according to claim 11, wherein the screwthreaded bore extends through the joint neck.

14. An endoprosthesis according to claim 1, wherein two oppositely situated clamping surfaces are formed on the shaft piece and between them an articulation chamber is formed to receive the articulation member.

15. An endoprosthesis according to claim 14, wherein a distance between the clamping surfaces is adjustable.

16. An endoprosthesis according to claim 15, wherein the shaft piece has a cover screwable on the shaft head.

17. An endoprosthesis according to claim 16, wherein the articulation chamber is formed in the shaft head.

18. An endoprosthesis according to claim 17, wherein the articulation chamber is formed in the cover.

19. An endoprosthesis according to claim 3, wherein the articulation surface is formed by a number of edges.

20. An endoprosthesis according to claim 19, wherein the articulation surfaces of the articulation member which are situated opposite one another in a direction of the joint neck axis are formed differently.

21. An endoprosthesis according to claim 20, wherein at least one articulation surface has substantially a conical shape.

22. An endoprosthesis according claim 20, wherein at least one articulation surface has substantially a cylindrical shape.

23. An endoprosthesis according to claim 20, wherein at least one articulation surface has substantially a toroidal shape.

24. An endoprosthesis according to claim 20, wherein at least one articulation surface has a corrugated surface.

25. An endoprosthesis according to claim 20, wherein the shaft piece has a first clamping means by which the articulation member can be pressed against the shaft piece.

26. An endoprosthesis according to claim 20, wherein a screwthreaded bore extends through the articulation member and a screw can be screwed therethrough as a second clamping means.

* * * * *